United States Patent [19]

Maxwell

[11] 4,033,903
[45] July 5, 1977

[54] PROCESS FOR PREPARING MODIFIED SILVER CATALYSTS

[75] Inventor: Ian E. Maxwell, Haarlem, Netherlands

[73] Assignee: Shell Oil Company, Houston, Tex.

[22] Filed: Apr. 19, 1976

[21] Appl. No.: 678,106

[30] Foreign Application Priority Data

Mar. 25, 1976 United Kingdom ............ 12129/76

[52] U.S. Cl. ............................................ 252/476
[51] Int. Cl.$^2$ ......................................... B01J 23/50
[58] Field of Search ........................... 252/463, 476

[56] References Cited

UNITED STATES PATENTS

| 2,671,764 | 3/1954 | Sacken ..................... 252/476 X |
| 3,563,914 | 2/1971 | Wattimena ..................... 252/463 |
| 3,962,136 | 6/1976 | Nielsen et al. ................. 252/476 X |

*Primary Examiner* — W. J. Shine

[57] ABSTRACT

Silver catalysts providing improved selectivities for the oxidation of ethylene to ethylene oxide are prepared by (a) subjecting a catalyst comprising from about 1 to about 35 percent by weight of silver on a porous refractory catalyst support to a stabilization treatment, and (b) depositing from about 0.00004 to about 0.008 gram equivalent weights per kilogram of total catalyst of ions of one or more of the alkali metals potassium, rubidium or cesium on the stabilized catalyst.

2 Claims, No Drawings

PROCESS FOR PREPARING MODIFIED SILVER CATALYSTS

BACKGROUND OF THE INVENTION

1. Field of the Invention

The invention relates to a process for preparing modified silver catalysts which can be used in oxidation processes, especially in a process for the production of ethylene oxide by direct oxidation of ethylene with molecular oxygen.

2. The Prior Art

Catalysts comprising from 1 to 35% by weight of silver on a porous refractory support are known to be useful for the production of ethylene oxide by the controlled incomplete oxidation of ethylene with molecular oxygen. A great variety of modifications have been proposed to improve the activity and selectivity of silver catalysts. The modifications have involved, for example, the supports employed, the method of production, the physical form of the silver on the support, and the addition of certain additives to the catalyst.

It has been observed that the selectivity of silver catalysts may change during the initial period of their use in the manufacture of ethylene oxide. The selectivity of some catalysts increases during this period of operation, and then remains constant for a long period of time, whereas the selectivity of other catalysts gradually decreases, and then remains constant or fairly constant. The applicants have found that this change in initial activity is probably due to stabilization of the silver catalyst taking place during the initial period of their use.

It is known from British patent specification No. 1,413,251 that the addition of from 0.00035 to 0.0030 grams equivalent weights per kilogram (based on the entire catalyst) of ions of one or more of the alkali metals potassium, rubidium or cesium, coincidentally with the deposit of silver on the catalyst support results in an improved selectivity of the catalyst thus obtained. According to this British patent specification the alkali metal and the silver are deposited coincidentally on the catalyst support since in this way catalysts having optimum selectivity (75–81%) are obtained. From Example VII of British patent specification No. 1,413,251 it appears that when potassium is deposited on the support after the deposition of the silver, the selectivity improvement is smaller than that obtained by simultaneous deposition of silver and alkali metal. The silver catalyst used in this example was prepared by impregnating a support with a solution of a silver oxalate complex followed by heating in order to reduce the silver salt to silver metal. This silver catalyst showed a selectivity of 69%. After the treatment with the potassium-containing solution the selectivity was increased to 73–74%, which is clearly less than the optimum mentioned above.

Hoechst, Inc., filed a German patent application on May 2, 1975, now issued as German Pat. No. 2,519,599, July 1, 1976 which discloses a process in which so-called "tired" silver catalysts which have been used for the manufacture of ethylene oxide for a long period of time are soaked with an impregnating solution consisting of (1) 0.2 to 5%w of water, (2) 0.05 to 0.4%w of cesium or rubidium nitrate, and (3) an aliphatic alcohol having 1 to 3 carbon atoms, and the alcohol is subsequently removed at a temperature between 70° and 120° C, preferably between 90° and 110° C, optionally with blowing through of nitrogen. There is no indication that other solvents or anions other than nitrate are operative.

SUMMARY OF THE INVENTION

According to the present invention a process for preparing modified silver catalysts comprises (a) subjecting a catalyst comprising from 1 to 35% by weight (based on the entire catalyst) of silver on a porous refractory catalyst support to a stabilization treatment, and (b) depositing from 0.00004 to 0.008 gram equivalent weights per kilogram (based on the entire catalyst) of ions of one or more of the alkali metals potassium, rubidium or cesium on the stabilized catalyst, cesium and rubidium ions being preferred. The particular anion associated with the ions of potassium, rubidium or cesium is not critical. Acetates, carbonates, bicarbonates and chloride have been found to produce good results.

DESCRIPTION OF THE PREFERRED EMBODIMENTS

The applicants have investigated the effect on the ethylene oxide selectivity of deposition of alkali metals on silver catalysts prepared by many methods, for example by impregnation of a support with a solution of silver nitrate followed by reduction with hydrogen. Such a catalyst typically shows a rapid intial improvement in activity and selectivity over a period of approximately one day followed by a slow continuation of the performance improvement until after approximately 1 month a stabilized catalyst is obtained giving a selectivity of approximately 69–70% at an oxygen conversion of 40%. This performance is normally maintained for a period of many years. When cesium is deposited on a freshly prepared catalyst of this type the selectivity attained after stabilization has taken place is only 1–2% higher than that attained with the stabilized undoped catalyst.

It has now been found that when freshly prepared catalysts of this type have been stabilized by using them in the production of ethylene oxide for a period of time sufficiently long to enable the selectivity to become constant or fairly constant (1–4 weeks) or by subjecting them to a heat treatment as described below, deposition of potassium, rubidium or cesium gives a much larger improvement of the selectivity (up to 6% and more).

According to the present invention a process for preparing modified silver catalysts comprises (a) subjecting a catalyst comprising from 1 to 35% by weight (based on the entire catalyst) of silver on a porous refractory catalyst support to a stabilization treatment, and (b) depositing from 0.00004 to 0.008 gram equivalent weights per kilogram (based on the entire catalyst) of ions of an alkali metal selected from the group consisting of potassium, rubidium, cesium, or mixtures thereof on the stabilized catalyst, cesium and rubidium ions being preferred.

It has been found that the size of the silver particles present in the catalyst usually changes during the initial period of use of the catalyst in the manufacture of ethylene oxide. Larger silver particles having a diameter of, for example, 4 microns break up into smaller particles which are more stable under the reaction conditions used, whereas small silver particles having a diameter of, for example, 0.1 micron sinter to form more stable larger particles. The stable particle size is thought to be determined by the surface tension under the reaction conditions used during ethylene oxide manufacture. The diameter of the stable silver particles is usually distributed between 0.2 and 4 microns, particularly between 0.4 and 2.5 microns, but as pointed out, it depends on the reaction conditions used. It has been found that the changes in size of the silver particles during the initial period of the use of the catalyst contribute significantly to the changes in activity and selectivity of the catalyst usually observed in that period.

Catalysts prepared by impregnation of a support with silver nitrate followed by hydrogen reduction usually contain larger (2-4 microns) particles. As mentioned above, the process of the invention is very suitable for improving the selectivity of such catalysts. However, the process is also of value for improving silver catalysts prepared by other methods, for example, by impregnation of a support with a solution of a silver salt of a carboxylic acid followed by thermal reduction of the silver salt to silver, such as, for example, the catalyst used in Example VII of British patent specification No. 1,413,251. Such silver catalysts may contain silver in the form of 0.1-1 micron particles. the selectivity of these catalysts may initially be high, for example 78% or more, but it gradually decreases during use of the catalyst. This is at least partially due to sintering of the smaller (e.g. 0.1 micron) silver particles. When according to the present invention such catalysts are stabilized before the potassium, rubidium or cesium is deposited thereon, they are more capable of maintaining optimum selectivity during use than catalysts obtained by depositing one or more of the said alkali metals on the freshly prepared silver catalysts.

Thus, the stabilization treatment which is used in the process of the invention may consist in using the silver catalyst for the oxidation of ethylene with molecular oxygen until the selectivity to ethylene oxide has become constant or fairly constant. The time necessary for stabilizing the catalyst varies considerably depending upon the catalyst used and the reaction conditions applied. However, if desired, the catalyst may be used for a longer period of time than that required for reaching stability. Even silver catalysts which have been used in the manufacture of ethylene oxide for many years can be considered to be catalysts which have been subjected to a stabilization treatment as required by step (a) of the process of the invention. Thus, the invention also includes a method for improving the selectivity of used silver catalysts by depositing from 0.00004 to 0.008 gram equivalent weights per kilogram (based on the entire catalyst) of ions of one or more of the alkali metals potassium, rubidium or cesium on such catalysts.

The stabilization treatment which is applied in step (a) of the process of the invention may also consist of subjecting a freshly prepared catalyst or a catalyst which has not yet been completely stabilized to a heat treatment other than simply using the catalyst. This treatment comprises heating the catalyst at an elevated temperature preferably between 150° and 900° C, most preferably between 200° and 800° C. The heating should preferably be continued until the major part of the silver particles present in the catalyst have reached a size distribution which approximates to that which is stable under the reaction conditions used in the manufacture of ethylene oxide. This stable particle size distribution can easily be determined by means of electron photomicrographs. When the preparation of ethylene oxide is carried out under the preferred conditions indicated below in this application, the diameter of the stable silver particles is usually between 0.2 and 4 microns, particularly between 0.4 and 2.5 microns.

The stabilization is attained in a shorter period of time when the heat treatment is carried out at higher temperatures. For example, good results are obtained by heating the catalyst during 5-20 hours at a temperature between 400° and 750° C. The heating may be carried out in the presence of an inert gas, such as for example nitrogen, or an oxygen-containing gas, such as, for example, air. This gas may be continuously passed over the catalyst. In some cases it may be advantageous to carry out the heating in the presence of an atmosphere containing ethylene and/or one or more compounds which are usually employed as moderating agents in the manufacture of ethylene oxide, for example, 1,2-dichloroethane, vinyl chloride or chlorinated polyphenyl compounds.

Any silver catalyst suitable for the manufacture of ethylene oxide and containing from 1 to 35%, preferably 1-25%, by weight (based on the entire catalyst) of silver on a porous refractory support may be used as starting material in the process of the invention. Such catalysts can be obtained, for example, by impregnating the support with an aqueous solution of silver nitrate, drying and reducing with hydrogen or hydrazine as described in U.S. Pat. No. 3,575,888. In other techniques the support may be impregnated with an aqueous solution of a silver salt of an organic carboxylic acid, such as, for example, lactic acid followed by heating in order to decompose the deposited silver salt as described in U.S. Pat. No. 3,725,307 or the support may be impregnated with an ethanolamine-containing solution of a silver salt and then reduced as disclosed by Japanese patent specification No. 19,606/1971. Alternatively, a slurry of the oxide or hydroxide of silver may be deposited on the support followed by drying and reduction with hydrogen. The support may also be treated with a suspension of silver oxide in an aqueous solution of a water-soluble silver salt of an organic acid capable of reducing silver oxide to metallic silver, for example, lactic acid, and subsequently heated as described in British patent specification No. 1,351,299. According to U.S. Pat. No. 3,043,854 a slurry of fine particles of silver carbonate is added to the support followed by thermal decomposition. In another method silver is used to the support in the form of "cluster" silver as described in U.S. Pat. No. 3,781,317. An effective method described in British patent specification No. 1,369,639 comprises adding to the support an aqueous solution containing a silver salt of a carboxylic acid, a vicinal ethylene amine and/or a vicinal alkanolamine, and, optionally ammonia, drying and reducing the silver salt to silver by heating.

The support employed in the silver catalysts can be selected from the large number of conventional, porous, refractory catalyst carriers or support materials which are essentially inert in the presence of the ethylene oxidation feeds, products and reaction conditions. Such conventional materials may be of natural or synthetic origin and preferably are of a macroporous structure, that is, a structure having a surface area below 10 $m^2/g$ and preferably below 2 $m^2/g$. These support materials typically have an apparent porosity of greater than 20%. Very suitable supports comprise those of siliceous and/or aluminous compositions. Specific examples of suitable supports are the aluminum oxides (including the materials sold under the trade name "Alundum"), charcoal, pumice, magnesia, zirconia, kieselguhr, fuller's earth, silicon carbide, porous agglomerates comprising silicon and/or silicon carbide, silica, magnesia, selected clays, artificial and natural zeolites and ceramics. Particularly useful refractory supports comprise the aluminous materials, in particular those containing alpha-alumina. In the case of alpha-alumina-containing supports, the specific surface area as measured by the B.E.T. method may be, for example, between 0.03 $m^2/g$ and 2.0 $m^2/g$ and the apparent porosity as measured by conventional mercury or water absorption techniques may be, for example, between 25 and 65%. The B.E.T. method for determining specific surface area is described in detail in Brunauer, S., Emmet, P.H., and Teller, E., *J. Am. Chem. Soc.*, 60, 309–16 (1938). Specific examples of suitable supports are the supports marketed by Norton Company as "Alundum" grades LA-956, SA-5556, LA-4118, and SA-101, or their equivalents.

Regardless of the character of the support used, it is preferably shaped into particles, chunks, pieces, pellets, rings or spheres of a size suitable for employment in fixed-bed applications. Conventional commercial fixed-bed ethylene oxidation reactors are typically in the form of a plurality of parallel elongated tubes (in a suitable shell) approximately 2.0 to 5 cm in diameter and 5 to 14 meters long, filled or partly filled with catalyst. In such reactors, it is desirable to employ a support formed into a rounded shape, such as, for example, spheres, pellets, rings or tablets having diameters of from approximately 0.25 to 2.0 cm.

The ions of potassium, rubidium and/or cesium can be deposited on the silver catalyst by impregnating it with a solution of one or more compounds of these alkali metals in a suitable solvent, particularly an organic solvent. Examples of suitable compounds are the hydroxides, chlorides, iodides, bromides, bicarbonates, and carbonates of potassium, rubidium or cesium or organic derivatives of these alkali metals, for example, their alkoxides, such as the isopropoxides, or their salts with organic carboxylic acids, such as, for example, the acetates, oxalates, tartrates and lactates. Suitable solvents are, for example, methanol, ethanol, isopropanol, acetone, methyl acetate and tetrahydrofuran. If desired, the solubility of the alkali metal compounds in the solvent may be increased by the use of complexing agents, such as, for example, macrocyclic polyethers of the type described in British patent specifications Nos. 1,108,921 and 1,285,367. The organic solvent may contain water in order to increase the solubility of the alkali metal compound in the solvent. However, with some salt-solvent combinations the presence of high concentrations of water may be deleterious to the ultimate performance so that the amount of water present in the solvent is preferably no more than 20% by weight, most preferably no more than 10% by weight. Methanol and ethanol are preferred solvents. The amount of the impregnating solution and the concentration of the alkali metal therein should be sufficient to deposit 0.00004 and 0.008, preferably between 0.0001 and 0.002 gram equivalent weights per kilo of total catalyst of the alkali metal on the catalyst.

After the impregnation with the solution of alkali metal compound(s), the excess of solvent should be removed. This can be done at atmospheric, sub- or superatmospheric pressure. The catalyst may be heated at a temperature above the boiling point of the solvent used, for example, a temperature between 60° and 200° C, for a time between, for example, 0.5 and 24 hours, particularly between 2 and 16 hours. During the drying treatment a gas such as, for example, nitrogen, air, hydrogen, noble gases, carbon dioxide, methane or mixtures of these gases may be passed over the catalyst. Freeze-drying or drying in vacuum at room temperature or elevated temperature may also be used.

If desired, the process of the invention may be carried out in the reactor used for the manufacture of ethylene oxide. For example, a solution of one or more compounds of potassium, rubidium and/or cesium may be passed through the reactor containing silver catalyst which has been used in the manufacture of ethylene oxide for a period of time sufficiently long to stabilize it, and then the excess of solvent may be removed by passing a gas, for example, nitrogen, at a temperature above the boiling point of the solvent of the impregnating solution over the catalyst. Alternatively, fresh silver catalyst may be stabilized in the ethylene oxide reactor by a suitable heat treatment other than using the catalyst, as described above, and then the solution of the alkali metal compound may be passed through the reactor followed by removal of the solvent.

The modified silver catalysts according to the invention are useful for the production of ethylene oxide by contacting ethylene in the vapor phase with a molecular oxygen-containing gas at a temperature of from 150°–300° C, preferably 190°–285° C, most preferably 210 to 275° C in the presence of such a catalyst. The conditions for carrying out such an oxidation reaction in the presence of the silver catalysts of the present invention broadly comprise those described in the prior art. This applies, for example, to suitable temperatures, pressures, residence times, diluent materials such as nitrogen, carbon dioxide, steam, argon, methane or other saturated hydrocarbons, the presence or absence of moderating agents to control the catalytic action, for example, 1,2-dichloroethane, vinyl chloride or chlorinated polyphenyl compounds, the desirability of employing recycle operations or applying successive conversion in different reactors to increase the yields of ethylene oxide, and any other special conditions which may be selected in processes for preparing ethylene oxide. Pressures in the range of from about atmospheric to about 500 psi are generally employed. Higher pressures may, however, be employed within the scope of the invention. Molecular oxygen employed as reactant is obtained from conventional sources. The suitable oxygen charge may consist essentially of relatively pure oxygen, a concentrated oxygen stream comprising oxygen in major amounts with lesser amounts of one or more diluents such as nitrogen, argon, etc., or another oxygen-containing stream such as air. The use of the present modified silver catalysts in ethylene oxidation reactions is in no way limited to the use of specific conditions among those which are known to be effective.

In a preferred application of the modified silver catalysts of the invention, ethylene oxide is produced by contacting an oxygen-containing gas (containing at least 95% oxygen) together with ethylene, a diluent gas and a moderator, with a catalyst according to the invention at a temperature in the range of from 190° C to 285° C, and preferably 210° C to 275° C.

The resulting ethylene oxide is separated and recovered from the reaction products by conventional methods.

The preparation of midified silver catalysts according to the present invention as well as their use in the production of ethylene oxide will be further described by the following examples which are provided for illustration and are not to be construed as limiting the invention.

EXAMPLE I

A silver catalyst which had been used for 8.5 years in the manufacture of ethylene oxide on a commercial scale was used as starting material for the preparation of catalysts A-P described in this Example. The silver catalyst contained 10.5% by weight of silver deposited on a support sold by Norton Company under the trade name "Alundum", grade SA-101 comprising 90.4% by weight of alpha-alumina, 8.5% by weight of $SiO_2$ and 1.1% by weight of other metal oxides, by impregnation of the support with an aqueous silver nitrate solution followed by drying, and reduction with hydrogen. The support had the form of hollow cylinders approximately 8.0 mm in diameter and approximately 8mm long. It had a specific surface area of 0.05 m²/g, an apparent porosity of 43 to 47% by volume, and a median pore diameter of 25 microns. The diameter of the silver particles present in this catalyst was in the range between 0.4 to 2 microns. the original, freshly prepared catalyst contained silver in the form of 2-4 microns particles.

By measuring the water absorption of the silver catalyst its pore volume was determined. It amounted to 0.144 ml/g. Impregnating solutions of the cesium, rubidium and potassium compounds indicated below in Table I, were prepared containing the alkali metal compound in such a concentration that after soaking of the silver catalyst with the solution the desired amount of alkali metal compound was present in the solution retained by the pores after draining off the excess solution. An amount of 100g of catalyst was soaked with 100 ml of impregnating solution for a period of at least 10 minutes. After draining off the excess solution, the catalyst was dried in an oven at 120° C for 17 hours or in a vacuum drying apparatus at a pressure of 0.2 mm Hg at room temperature (20° C).

The specific conditions used in the preparation of the catalysts have been summarized at Table I. The starting catalyst similar to the one used in the preparation of catalysts A-P, but which had not been used in the manufacture of ethylene oxide. In the preparation of catalyst Y the same fresh silver catalyst was first used during 140 hours for the manufacture of ethylene oxide whereafter the cesium compound was deposited thereon.

TABLE 1

| Catalyst | Alkali metal compound | Conc. of alkali metal ion in impregnating solution in mg/100 ml | Solvent used in preparing impregnating solution | Conc. of alkali metal ion on catalyst in ppm | Drying conditions |
|---|---|---|---|---|---|
| A | Cs-acetate | 49.4 | abs. ethanol | 50 | 17 hrs at 120° C |
| B | Cs-acetate | 49.4 | acetone-2% v $H_2O$ | 50 | 3 hrs at 120° C |
| C | Cs-acetate | 49.4 | abs. ethanol | 50 | 17 vacuum at 20° C |
| D | Cs-acetate | 49.4 | ethanol-10% v $H_2O$ | 50 | 17 hrs at 120° C |
| E | $CsNO_3$ | 50 | methanol-0.5% v $H_2O$ | 50 | 17 hrs at 120° C |
| F | $CsNO_3$ | 100 | methanol-0.5% v $H_2O$ | 100 | 17 hrs at 120° C |
| G | $Cs_2CO_3$ | 41.7 | methanol-0.5% v $H_2O$ | 50 | 17 hrs at 120° C |
| H | $CsHCO_3$ | 50 | methanol-0.5% v $H_2O$ | 50 | 17 hrs at 120° C |
| I | $CsHCO_3$ | 100 | methanol-0.5% v $H_2O$ | 100 | 17 hrs at 120° C |
| K | $CsHCO_3$ | 50 | acetone-3.5% $H_2O$ | 50 | 17 hrs at 120° C |
| L | CsCl | 43.2 | abs. ethanol | 50 | 17 hrs at 120° C |
| M | $Rb_2CO_3$ | 29.5 | abs. methanol | 32 | 17 hrs at 120° C |
| N | $RbNO_3$ | 75.6 | methanol-0.5% $H_2O$ | 64 | 17 hrs at 120° C |
| O | Rb-acetate | 37.1 | abs. methanol | 32 | 17 hrs at 120° C |
| P | K-acetate | 25.1 | abs. methanol | 15 | 17 hrs at 120° C |
| X | $CsNO_3$ | 100 | methanol-0.5% $H_2O$ | 100 | 17 hrs at 120° C |
| Y | Cs-acetate | 49.4 | abs. ethanol | 50 | 1.5 hrs at 120° C |

The doped catalysts indicated in Table I and the undoped catalyst were tested for the production of ethylene oxide by charging them in a reactor tube with an internal diameter of 2 cm and a bed length of 20 cm. A gas mixture consisting of 25%m of ethylene, 8%m of oxygen, 0.5-2 ppm of dichloroethane and the remainder nitrogen, was passed over the catalyst at a pressure of 1 atmosphere, and a gas hourly space velocity of 250 $hr^{-1}$.

The ethylene oxide selectivity attained at the indicated oxygen conversion and the temperature required to attain that oxygen conversion are summarized in Table II.

TABLE II

| Catalyst | Ethylene oxide selectivity %m | Oxygen conversion %m | Temperature ° C |
|---|---|---|---|
| Undoped | 75.2 | 9 | 234 |
| Undoped | 73 | 20 | 253 |
| Undoped | 70.6 | 32 | 263 |
| Undoped | 67.3 | 50 | 273 |
| A | 79.7 | 10 | 235 |
| A | 78 | 20 | 251 |
| A | 73.4 | 44 | 274 |

TABLE II-continued

| Catalyst | Ethylene oxide selectivity %m | Oxygen conversion %m | Temperature °C |
|---|---|---|---|
| B | 77.3 | 9 | 240 |
| B | 74.9 | 22 | 260 |
| B | 72 | 34 | 274 |
| C | 79.7 | 7.5 | 230 |
| C | 78.3 | 14.5 | 246 |
| C | 73.1 | 47 | 276 |
| D | 79.5 | 10 | 240 |
| D | 78.3 | 17 | 249 |
| D | 76.7 | 30 | 259 |
| E | 78.5 | 8 | 205 |
| E | 77.6 | 19 | 223 |
| E | 74.8 | 43 | 253 |
| F | 78.8 | 8.5 | 204 |
| F | 76.9 | 30 | 245 |
| F | 74.5 | 47 | 259 |
| G | 79.8 | 10 | 232 |
| G | 78.2 | 20 | 246 |
| G | 74.6 | 42 | 269 |
| H | 80.1 | 8 | 230 |
| H | 78.6 | 18 | 247 |
| H | 74.4 | 45 | 268 |
| I | 76.6 | 14 | 251 |
| I | 73 | 26 | 267 |
| K | 78.6 | 9 | 233 |
| K | 77 | 17.5 | 249 |
| K | 75.1 | 28 | 261 |
| L | 78 | 15 | 252 |
| L | 73.1 | 39 | 277 |
| M | 79 | 9 | 238 |
| M | 77.8 | 14 | 243 |
| M | 73.6 | 36 | 269 |
| N | 75.3 | 18 | 242 |
| N | 72.2 | 38 | 273 |
| O | 77.7 | 10 | 240 |
| O | 76 | 18 | 253 |
| O | 73 | 36 | 273 |
| P | 77.8 | 6 | 238 |
| P | 75.6 | 16 | 253 |
| P | 70.2 | 43 | 277 |
| X | 75.8 | 12 | 262 |
| X | 73.1 | 26 | 284 |
| Y | 77.5 | 9 | 223 |
| Y | 76 | 17 | 242 |
| Y | 73.7 | 32 | 261 |
| Y | 70.8 | 50 | 277 |

EXAMPLE II

Catalyst Q was prepared as follows. As support for the catalyst was employed Norton Company's Alundum, Grade LA-5556, in the form of hollow cylinders approximately 8 mm in diameter and approximately 8 mm long. This support contained 99.3% by weight alpha-alumina, 0.4% silica, and 0.3% of other metal oxides, and had a surface area of 0.24 m²/g and an apparent porosity of 48–49% by volume. The support had a median pore diameter of 4.4 microns as determined by mercury porosimetry, 81% of its pores had diameters in the range of from 1.5 to 15 microns.

A solution of 118.3g $AgNO_3$ in 75 ml of water was mixed with a solution of 51.2g sodium oxalate in 833 ml $CO_2$ free water at a temperature of 80° C. Water was added until the total volume of the mixture was 1167 ml, and the mixture was maintained at a temperature of 80° C for 30 minutes. It was then cooled to 50° C, decanted, and 167 ml of $CO_2$-free water were added to the remaining slurry. The silver oxalate was filtered off and washed five times with 167 ml of $CO_2$-free water until the effluent was sodium-free. The filter cake was suspended in 167 ml of water and the suspension was cooled with ice-water. The impregnating solution was then prepared by mixing the suspension with 50 ml of ethylene diamine and 16.7 ml of monoethanolamine.

An amount of 500g of support was impregnated twice with the impregnating solution, and after the solution was drained off, the support was dried at 200° C for 5 hours. The dried support was then soaked again with the impregnating solution, and after the excess solution was drained off the support was dried at 200° C for 18 hours.

The catalyst obtained contained 12.5% weight of silver. The diameter of the silver particles present in catalyst Q was examined by electron microscope and found to be between approximately 0.1 and 0.2 microns.

Catalyst R was prepared by impregnating catalyst Q with a sulution containing 49.4mg of Cs-acetate in 100 ml of ethanol by means of the method described in Example I. The catalyst was dried at a temperature of 120° C during 17 hours. It contained 50 ppm of cesium.
Catalyst S was prepared by heating catalyst Q at a temperature of 700° C during 16 hours. The diameter of the silver particles present in catalyst S was found to be between 0.5 and 2 microns.

Catalyst T was prepared by impregnating catalyst S with a solution containing 49.4 mg of Cs-acetate in 100 ml ethanol by means of the method described in Example I. The catalyst was dried at a temperature of 120° C during 5 hours. It contained 50 ppm of cesium.

Catalysts Q, R, S and T were tested for the production of ethylene oxide in the same way as the catalysts described in Example I. The mixture of ethylene, oxygen and nitrogen contained 1.7 ppm of dichloroethane.

The ethylene oxide selectivity attained at the indicated oxygen conversion and the temperature required to attain that oxygen conversion are summarized in Table III.

TABLE III

| Catalyst | Ethylene Oxide Selectivity %m | Oxygen Conversion %m | Temperature °C |
|---|---|---|---|
| Q | 83.2 | 13 | 204 |
| Q | 81.5 | 22 | 217 |
| Q | 79.5 | 39 | 229 |
| R | 82.2 | 14 | 204 |
| R | 80.9 | 25.5 | 217 |
| R | 79.4 | 38 | 232 |
| S | 78.8 | 6 | 243 |
| S | 75.5 | 16 | 261 |
| S | 70 | 41 | 271 |
| S | 67 | 49 | 277 |
| T | 82 | 10 | 220 |
| T | 81 | 20 | 235 |
| T | 77.8 | 46 | 250 |

I claim as my invention:
1. A process for preparing modified silver catalyst which comprises
   (a) heating a catalyst comprising from about 1 to about 35 percent by weight of the total catalyst of silver on a porous refractory support to a temperature between about 150° C to about 900° C;
   b. impregnating the catalyst of step (a) with a solution comprising a solvent and a salt of an alkali metal wherein the cation is selected from the group consisting of potassium, rubidium, cesium or mixtures thereof, and the anion is selected from the group consisting of hydroxides, chlorides, iodides, bromides, bicarbonates, carbonates, alkoxides, acetates, oxalates, tartrates and lactates, the amount of said salt being sufficient to deposit on said support from about 0.00004 to about 0.008 gram equivalent weight per kilogram of total catalyst of said alkali metal, and,
   c. removing said solvent from the impregnated support.
2. The process of claim 1 wherein the solvent is selected from the group consisting of methanol, ethanol, isopropanol, acetone, methyl acetate and tetrahydrofuran and wherein said solvents contain no more than 20 percent by weight of water.

* * * * *